(12) United States Patent
Morton et al.

(10) Patent No.: US 9,435,752 B2
(45) Date of Patent: Sep. 6, 2016

(54) SYSTEMS AND METHODS FOR SCANNING OBJECTS

(75) Inventors: Edward James Morton, Guildford (GB); Joseph Bendahan, San Jose, CA (US); Willem G. J. Langeveld, Menlo Park, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 523 days.

(21) Appl. No.: 13/577,178

(22) PCT Filed: Feb. 3, 2011

(86) PCT No.: PCT/GB2011/050182
§ 371 (c)(1),
(2), (4) Date: Dec. 28, 2012

(87) PCT Pub. No.: WO2011/095810
PCT Pub. Date: Aug. 11, 2011

(65) Prior Publication Data
US 2013/0129043 A1    May 23, 2013

(30) Foreign Application Priority Data
Feb. 3, 2010 (GB) .................................. 1001736.6

(51) Int. Cl.
*G01N 23/00* (2006.01)
*G01N 23/04* (2006.01)
*G01V 5/00* (2006.01)

(52) U.S. Cl.
CPC .............. *G01N 23/04* (2013.01); *G01V 5/0008* (2013.01)

(58) Field of Classification Search
CPC .... A61N 5/00–5/1043; G01N 23/00–23/2273
USPC ............................................................ 378/57
See application file for complete search history.

(56) References Cited

U.S. PATENT DOCUMENTS

| | | | |
|---|---|---|---|
| 3,919,467 A | 11/1975 | Peugeot | |
| 4,831,260 A | 5/1989 | Dibianca | |
| 4,998,270 A * | 3/1991 | Scheid | A61B 6/502 |
| | | | 378/145 |
| 5,040,199 A | 8/1991 | Stein | |
| 5,319,696 A | 6/1994 | Abdel-Malek | |
| 5,321,271 A | 6/1994 | Schonberg | |
| 5,418,372 A | 5/1995 | Schonberg | |

(Continued)

FOREIGN PATENT DOCUMENTS

| | | |
|---|---|---|
| EP | 0417965 | 3/1991 |
| JP | 2002014059 | 1/2002 |

(Continued)

OTHER PUBLICATIONS

Langeveld et al.: "Intensity-modulated Advanced X-ray Source (IMAXS) for Homeland Security Applications", IEEE Transactions on Nuclear Science, vol. 56, No. 3, Jun. 2009.*

(Continued)

*Primary Examiner* — Phillip A Johnston
(74) *Attorney, Agent, or Firm* — Novel IP

(57) ABSTRACT

The present application discloses scanner systems that have a radiation generator arranged to generate radiation to irradiate an object, a detector arranged to detect the radiation after it has interacted with the object and generate a sequence of detector data sets as the object is moved relative to the generator, and processors arranged to process each of the detector data sets thereby to generate a control output.

15 Claims, 8 Drawing Sheets

(56) References Cited

U.S. PATENT DOCUMENTS

| | | | |
|---|---|---|---|
| 5,661,377 | A | 8/1997 | Mishin |
| 5,838,759 | A | 11/1998 | Armistead |
| 5,909,478 | A | 6/1999 | Polichar |
| 5,949,811 | A | 9/1999 | Baba |
| 5,974,111 | A | 10/1999 | Krug |
| 6,438,201 | B1 | 8/2002 | Mazess et al. |
| 6,459,761 | B1 | 10/2002 | Grodzins |
| 6,504,898 | B1 * | 1/2003 | Kotler et al. .............. 378/64 |
| 6,507,027 | B1 * | 1/2003 | Kojima ............... B82Y 10/00 250/396 R |
| 6,713,773 | B1 | 3/2004 | Lyons et al. |
| 6,714,620 | B2 * | 3/2004 | Caflisch ............... A61N 5/103 378/65 |
| 7,010,094 | B2 | 3/2006 | Grodzins |
| 7,272,208 | B2 | 9/2007 | Yatsenko |
| 7,372,944 | B2 | 5/2008 | Bernhardt |
| 7,391,849 | B2 * | 6/2008 | Smith ............... A61N 5/1048 378/101 |
| 7,538,325 | B2 | 5/2009 | Mishin |
| 7,709,818 | B2 * | 5/2010 | Matsuda et al. .......... 250/492.3 |
| 8,054,937 | B2 | 11/2011 | Langeveld |
| 8,437,448 | B2 | 5/2013 | Langeveld |
| 8,781,067 | B2 | 7/2014 | Langeveld |
| 2003/0016790 | A1 * | 1/2003 | Grodzins et al. .......... 378/147 |
| 2003/0035510 | A1 | 2/2003 | Strommer |
| 2005/0117683 | A1 | 6/2005 | Mishin |
| 2005/0123101 | A1 * | 6/2005 | Akutsu et al. ............ 378/157 |
| 2006/0182221 | A1 | 8/2006 | Bernhardt |
| 2007/0140423 | A1 | 6/2007 | Foland |
| 2007/0147585 | A1 | 6/2007 | Eilbert |
| 2008/0211431 | A1 | 9/2008 | Mishin |
| 2010/0034355 | A1 | 2/2010 | Langeveld |

FOREIGN PATENT DOCUMENTS

| | | |
|---|---|---|
| JP | 2005149762 | 6/2005 |
| JP | 2007093501 | 4/2007 |
| WO | 0033060 A2 | 6/2000 |
| WO | WO0159485 | 8/2001 |
| WO | 2006000020 A1 | 1/2006 |
| WO | 2006053279 A2 | 5/2006 |
| WO | 2009000020 A1 | 12/2008 |
| WO | WO2009027667 | 3/2009 |
| WO | WO2009137698 | 12/2009 |
| WO | 2010019311 | 2/2010 |
| WO | 2011095810 A2 | 8/2011 |
| WO | WO2011095810 | 8/2011 |

OTHER PUBLICATIONS

Willem Gerhardus Johannes Langeveld et al., "Intensity Modulated Advanced X-Ray Source (IMAXS) for Homeland Security Applications", IEEE Transactions on Nuclear Science, IEEE Service Center, NY, NY US, vol. 56, No. 3, Jun. 1, 2009, pp. 1288-1291.
Examiiner Communication in GB1001736.6, dated Feb. 26, 2010.
International Search Report for PCT/GB2011/050182.
International Search Report for PCT/GB2011/050182, Dec. 28, 2011.
"Oral Program of SORMA West 2008", Jun. 5, 2008, pp. 1-95, XP055167963, Retrieved from the Internet: URL: http://www2.lbl.gov/conferences/SORMA/assets/doc/SORMAOralProgram30May.pdf.
Final Office Action for Japanese Application No. 2011523012, mailing date Jun. 19, 2014.
International Search Report for PCT/US09/47292, mailed on Apr. 23, 2012, Rapiscan Laboratories, Inc.
First Office Action for Chinese Application No. 2011800171264, dated Apr. 15, 2015.
SORMA West 2008 "Intensity Modulated Advanced X-Ray Source (IMAXS) for Homeland Security Applications", p. 74, [online], last updated: May 22, 2008. URL:http://www2.lbl.gov/conferences/SORMA/assets/doc/SORMAOralProgram30May.pdf.
Third Office Action for Japanese Patent Application No. JP2011523012, May 15, 2015.
Second Office Action for Chinese Application No. 2011800171264.
Third Office Action for Chinese Patent Application No. CN200980140400, Jun. 2015.

* cited by examiner

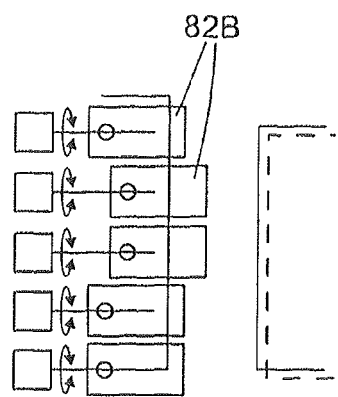
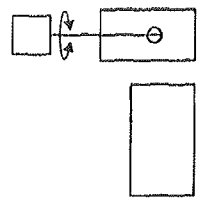
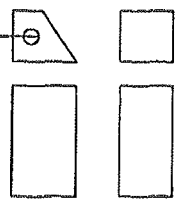
Fig. 8                Fig. 8a               Fig. 8b
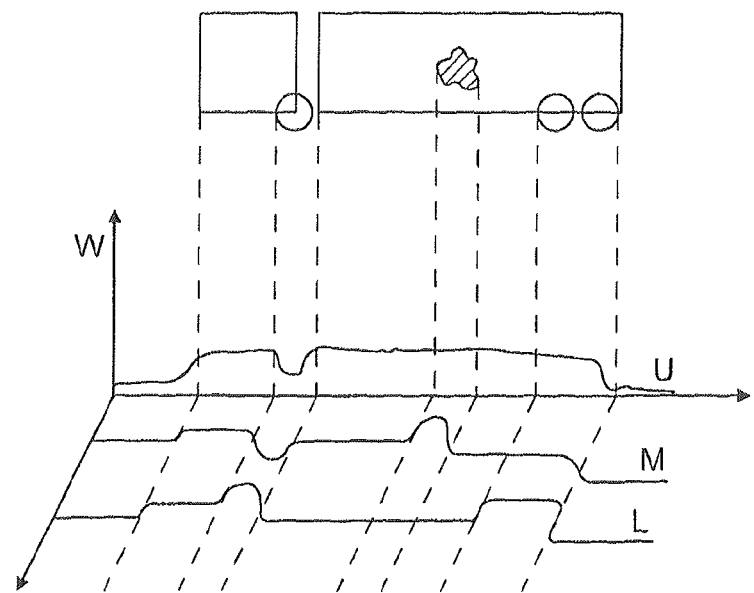
Fig. 9

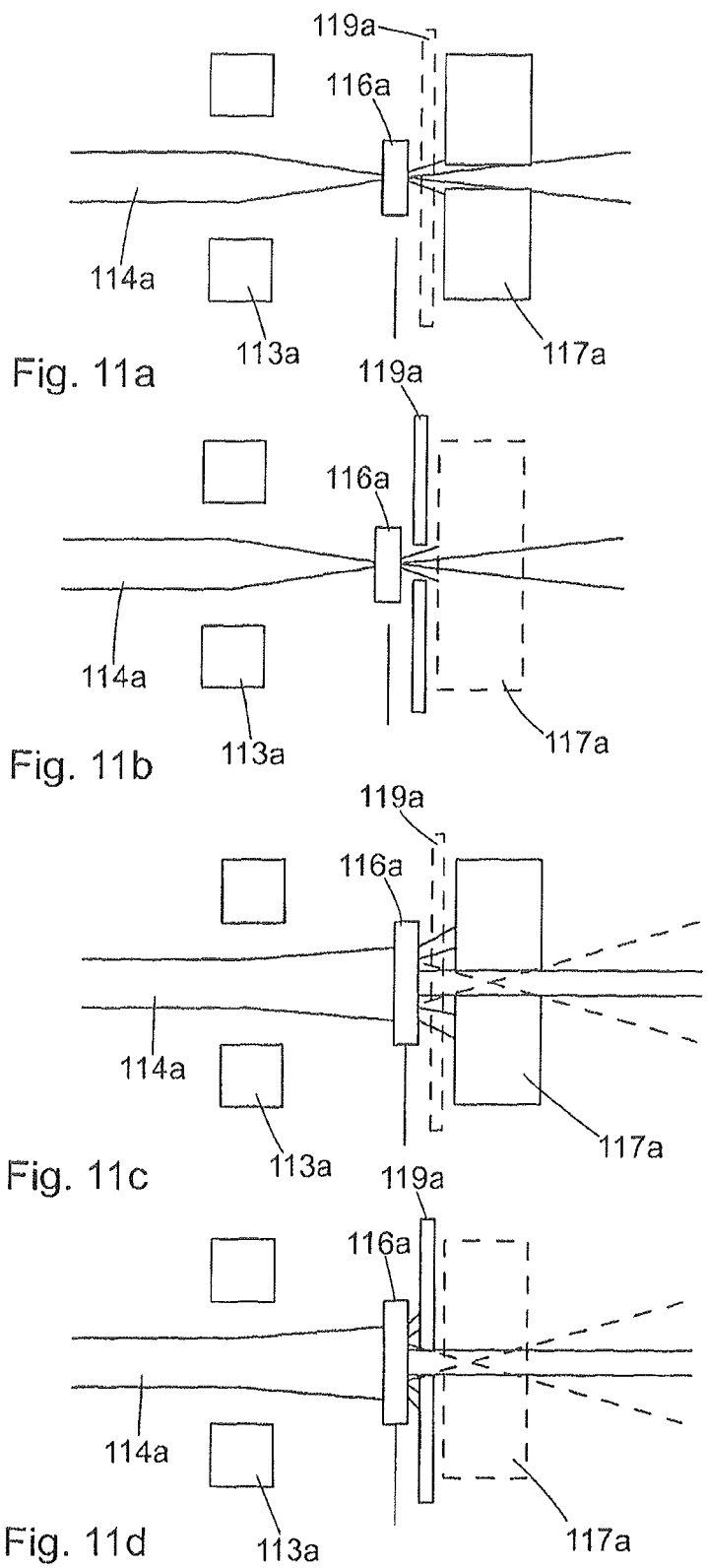

SYSTEMS AND METHODS FOR SCANNING OBJECTS

CROSS-REFERENCE

The present application is a national stage application of PCT/GB2011/050182, filed on Feb. 3, 2011, which relies on Great Britain Patent Application No. 1001736.6, filed on Feb. 3, 2010. All of the aforementioned applications are herein incorporated by reference.

FIELD

The present application relates to scanning systems, in particular to security scanning systems. It has particular application in the use of high energy X-radiation to inspect packages, cargo, containerised loads and vehicles for the presence of illicit materials and devices.

BACKGROUND

Given the increasing level of threat in the current climate, the use of X-ray imaging for inspecting all types of baggage and cargo is increasing. Although there is a benefit associated with X-ray scanning, there is also a detriment due to radiation dose to the object being inspected, to the operators of the radiation-producing scanning equipment, and to members of the public in the vicinity of the scanning equipment during operation. A good X-ray scanning system design shall seek to optimise image quality in order to provide a sufficient level of detection capability while simultaneously seeking to minimise the overall radiation dose that is delivered during scanning Currently known systems are generally designed in such a way that a single optimisation condition is used for all imaging, and this condition is generally the one which achieves maximum penetration performance, best spatial resolution and best contrast performance simultaneously for a given radiation footprint. Generally, penetration performance is optimised by selecting the energy of the X-ray source, spatial resolution is optimised by selecting the granularity of the X-ray detector, and contrast performance and penetration performance are optimised together through X-ray source output dose rate. Typically, collimation is used to provide a fan beam of radiation to constrain the X-ray beam to a narrow volume that extends from the X-ray source to cover some or all of the detection elements. This collimation acts to reduce X-ray scatter, and to further influence penetration, contrast performance and overall delivered radiation dose. The radiation footprint is determined by the maximum source output that delivers a regulatory dose to the public in the desired perimeter.

SUMMARY

The present invention provides a scanner system comprising a radiation generator arranged to generate radiation to irradiate an object, and detection means arranged to detect the radiation after it has interacted with the object and generate a sequence of detector data sets. The data sets may be generated as the object is moved relative to the generator. The system may further comprise processing means arranged to process each of the detector data sets thereby to generate a control output arranged to control the radiation generator, for example to vary its radiation output as the object is scanned.

The processing means may be arranged to define a parameter of the detector data. It may also be arranged to determine a value of the parameter for each data set. It may be arranged to generate a control output arranged to vary the radiation output if the value of the parameter does not meet a predetermined condition. The processing means may define a plurality of conditions and to vary the output in different ways, for example to increase or decrease the output, depending on which of the conditions is not met. The processing means may be arranged to keep the output constant if the condition is met, or all of the conditions are met.

The detection means may comprise a plurality of detectors. The detector data may comprise a set of intensity values, for example indicative of the intensity of radiation at each of the detectors.

The control output may be arranged to control the energy of the radiation. For example it may control the mean energy, or the energy distribution or spectrum of the radiation, or a maximum or minimum energy of the radiation.

The control output may be arranged to control a dimension of the radiation beam, such as its width, for example if it is a fan beam, or otherwise to control its cross sectional shape or area.

The radiation generator may be arranged to generate the radiation in pulses. The control output may be arranged to control at least one of the duration and the frequency of the pulses.

The radiation generator may comprise an adjustable collimator. The control input may be arranged to adjust the collimator in response to the control input. The collimator may have a varying thickness so that adjustment of the collimator can adjust the energy of the radiation beam. The collimator may comprise a plurality of collimator elements each of which may be adjustable independently so as to vary different respective parts of the radiation beam.

The radiation generator may comprise a collimator and the control input may be arranged to generate the radiation as a beam and to vary the position of the beam in response to the control input thereby to vary the proportion of the beam that is blocked by the collimator.

The radiation generator may comprise an electron source arranged to direct a beam of electrons towards a target. The radiation generator may be arranged to adjust the electron beam in response to the control input. The radiation generator may include a scraper arranged to block a variable proportion of the electrons in the beam. The radiation generator may be arranged to generate a magnetic field and to direct the electron beam through the magnetic field so that it turns. The magnetic field may be variable to vary the proportion of the electrons which are blocked. The radiation generator may be arranged to generate a variable magnetic field and to vary the magnetic field so as to vary focusing of the electron beam. This may be used in combination with a scraper to block a variable proportion of the electron beam, or a fixed collimator which can block a variable proportion of the X-rays depending on the focusing of the electron beam.

The processing means may be arranged to adjust the detector data to compensate at least partially for the controlled variation of the radiation output.

In general many embodiments of the invention relate to methods for reducing radiation dose during scanning to minimise dose to cargo, dose to operators and the radiation footprint of operating systems.

Some embodiments of the invention can provide an imaging system which is optimised to minimise radiation dose delivered to an object, and the surrounding exclusion zone, while maintaining a sufficient level of image quality by the means of real-time analysis of the image data that the imaging system is producing.

The invention relates, for example, to X-ray, gamma-ray and neutron producing imaging apparatus which may be operated in a number of ways including in a transmission mode, in a coherent scatter mode, in an incoherent scatter mode and/or in a backscatter mode.

Generally, imaging systems according to the invention can be designed in which the object is moved relative to a static imaging system or, in an alternative configuration, the static object is scanned by a moving imaging system. Particularly complex systems may require motion of both the object and the imaging system.

Preferred embodiments of the present invention will now be described by way of example only with reference to the accompanying drawings.

BRIEF DESCRIPTION OF THE DRAWINGS

FIG. 3b is a graph showing how dose rate is controlled based on the contents of the image of FIG. 3a;

FIG. 8 is a view similar to that of FIG. 2 showing a collimation system forming part of a scanner according to a further embodiment of the invention;

FIG. 8a is a plan view of the collimation system of FIG. 8;

FIG. 8b is a plan view of a further collimation system similar to that of FIG. 8;

FIG. 9 is a diagram showing how the width of upper, middle and lower collimators, and hence dose delivered at each point in the cargo, can be optimised in the system of FIG. 8 to match the required image quality characteristics;

DETAILED DESCRIPTION

Figure 1:
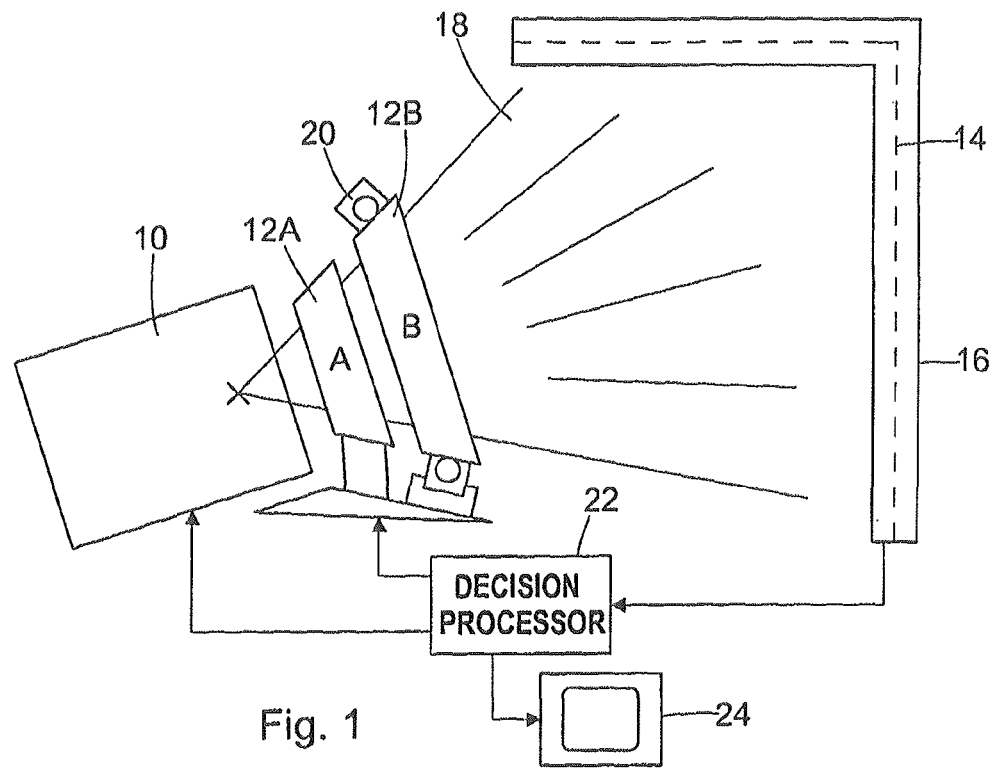
FIG. 1 is a schematic view of a radiation imaging system according to an embodiment of the invention.

Referring to FIG. 1, a scanner system comprises an X-ray beam generation system which includes a shielded radiation source 10, a primary collimator set 12A and a secondary collimator set 12B, and a set of radiation detectors 14 that in this example are configured into a folded L-shaped array 16.

The primary collimator set 12A acts to constrain the radiation emitted by the source 10 into a substantially fan-shaped beam 18. The beam 18 will typically have a fan angle in the range +/−20 degrees to +/−45 degrees with a width at the detector elements 14 in the range 0.5 mm to 50 mm. The second collimator set 12B is adjustably mounted and the position of the two second collimators 12B can be adjusted by means of actuators 20, under the control of a decision processor 22.

The detectors 14 output detector signals indicative of the radiation intensity they detect and these form, after conversion and processing described in more detail below, basic image data that is input to the decision processor 22. The decision processor 22 is arranged to analyse the image data and to control the actuators 20 to control the position of the second collimator set 12B in response to the results of that analysis. The decision processor 22 is also connected to a control input of the radiation source 10 and arranged to generate and vary a control signal it provides to the control input to control the energy and timing of X-ray pulses generated by the radiation source 10. The decision processor 22 is also connected to a display 24 on which an image of the imaged object, generated from the image data, can be displayed.

By way of example, the radiation source 10 may comprise a high energy linear accelerator with a suitable target material (such as tungsten) which produces a broad X-ray spectrum with a typical beam quality in the range from 0.8 MV to 15 MV from a relatively small focal spot typically in the range 1 mm to 10 mm diameter. The radiation source 10 in this case would be pulsed with a pulse repetition frequency generally in the range 5 Hz to 1 kHz where the actual rate of pulsing is determined by the decision processor 22.

The detectors 14 in this case are advantageously fabricated from a set of scintillation crystals (generally high density scintillator such as CsI, CdWO4, ZnWO4, LSO, GSO and similar are preferred) which are optically coupled to a suitable light detector, such as a photodiode or photomultiplier tube. Signals from these detectors 14 converted to digital values by a suitable electronic circuit (such as a current integrator or transimpedance amplifier with bandwidth filtering followed by an analogue to digital converter) and these digital values of the sampled intensity measurements are transferred to the decision processor 22 for analysis.

The primary 12A and secondary 12B collimators in this case are advantageously fabricated from high density materials such as lead and tungsten.

Figure 2:
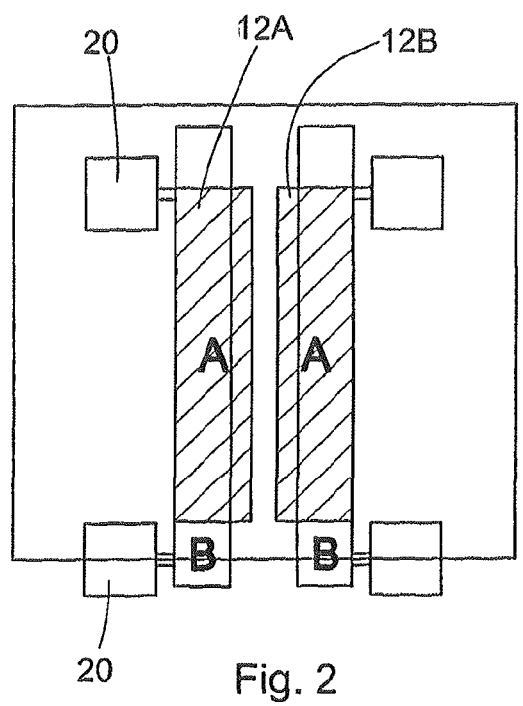
FIG. 2 is a view in the direction of the X-ray beam of the primary and secondary collimators of the system of FIG. 1.

In a first embodiment, as shown in FIG. 2, the secondary collimator 12B comprises two independently moveable jaws which normally lie substantially parallel to the primary collimator jaws 12A. The electronically controllable actuators 20 are located at the base and top of each secondary collimator jaw 12B and each arranged to move a respective end of the collimator jaw 12B. The four actuators 20 can therefore be operated independently to drive either end of either secondary collimator section 12B towards or away from the other secondary collimator section. The effect of this movement is to narrow or widen the secondary collimated radiation beam 18 as required. The impact of this is to modulate the radiation beam intensity, and how it varies as a function of position within the radiation fan beam 18, for example whether it increases or decease from the top to the bottom of the beam, and if so, at what rate.

The actuators 20 can be fabricated in many ways as will be apparent to one skilled in the art. However, suitable mechanisms, by way of example, include lead-screw assemblies in which an electric motor is used to turn a screw which engages on a threaded insert which is mounted on the collimator section. The collimator is pinned to a support frame such that it may move in and out towards the opposing collimator section but can not move up and down with respect to the radiation fan beam. As the lead-screw is rotated, the secondary collimator gap is varied as required. In a refinement of this mechanism, the threaded insert and motor assembly are each mounted to independent fixings which can rotate with respect to the collimator assembly such that as the collimator jaw moves in and out, the fixings rotate to prevent the lead-screw from binding in the threaded insert. In a further refinement, the lead-screw/motor assembly is provided with an absolute position encoder for precise measurement of the lead-screw/threaded insert position for direct feedback to the decision processor 22. Ideally the lead-screw would be fabricated from an easily machined and robust material such as stainless steel and the threaded insert from a different material, such as brass, to minimise screw thread binding which can occur if similar materials are used for both elements of the assembly.

Other suitable mechanisms for controlling the secondary collimators include electrical actuated solenoids, scissor mechanisms and so on.

In order to scan an object, the object is moved through the fan-shaped beam 18 with rows of transmission signal data from the detectors 14 being collected and stored periodically by the decision processor 22 so as to form a set of one-dimensional projections which are then combined into a two-dimensional image by simply stacking the one-dimensional projections side by side. It is good practice to modulate the rate at which the projection data is obtained so that it varies with the velocity of the object to be scanned relative to the radiation fan beam 18.

It will be appreciated that the secondary collimator 12B, which is formed of suitable radiation attenuating material, is arranged with a controlled motion system to allow precise positioning of the secondary collimator system 12B with respect to a fixed primary collimator assembly 12A. By finely adjusting the overlap between primary 12A and secondary 12B collimators, it is possible to adjust the dose rate so that it varies linearly over the height of the radiation fan beam 18 such that areas of the object with high attenuation can be provided with a high dose rate to maximise system dynamic range, while areas of low attenuation can be exposed to a low dose rate in order to minimise radiation dose while maintaining an acceptable level of image quality.

As shown in FIG. 1, image data from the radiation detectors 14 is passed to the decision processor block 22. The decision processor 22 is arranged, when it has received one linear image data set, which comprises one sample intensity value for each detector 14, to analyse that set of image data and determine suitable parameters from the data, such as number of samples with greater than threshold attenuation and number of samples with less than another threshold value. Based on the input data, the decision processor 22 is arranged to adjust the secondary collimator 12B settings, adjust the properties of the radiation source 10, and process the image for optimal display quality. Once the next sample set of data has been collected, the decision processor 22 determines the new optimal position settings for the secondary collimator 12B, energy and pulse timing settings for the radiation source 10, and optimal settings for the display processing, and the process continues as the object is scanned and more and more rows of image data are collected.

It will be appreciated that, while the control of the radiation source 10 is electronic and can be varied very quickly, the control of the position of the collimators requires operation of the actuators 20 and will therefore take place over longer timescales. Therefore, while the source may be controlled in response to each consecutive linear image data set, it may be necessary, if the sample rate is high, for the collimator position to be updated only after every two or more linear data sets have been collected.

Figure 3A:
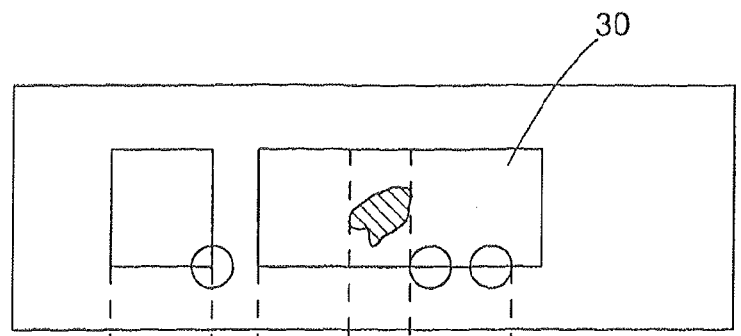
FIG. 3a shows an example of an X-ray image generated by the system of FIG. 1.
Figure 3B:
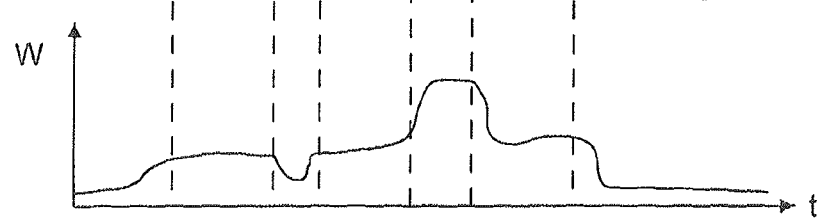

FIGS. 3a and 3b show how a radiation imaging system with the architecture described in FIG. 1 will operate when imaging an object 30 of varying composition. FIG. 3b shows how collimator width W is varied over time t, based on the composition of the object 30 under inspection, and image of which is shown in FIG. 3a. When there is nothing of interest in the beam, the collimator is narrowed down to a small width. Once the object 30 starts to appear in the image, the collimators are widened up enough to achieve a reasonable image quality. The secondary collimator width is varied continually, being narrower in regions of low attenuation and wider in regions of high attenuation where increased dose is required to maintain a satisfactory image quality.

Figure 4:
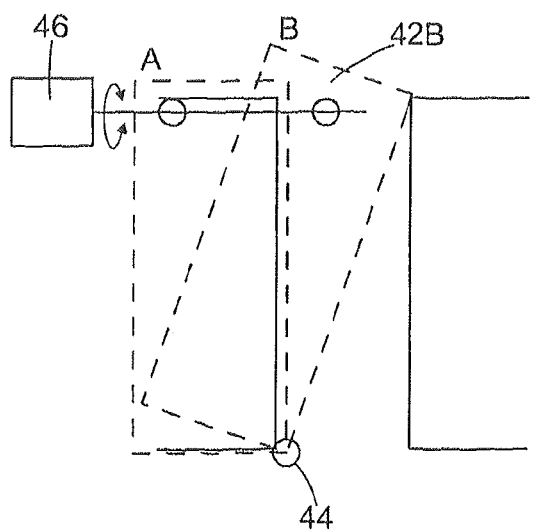
FIG. 4 is a view similar to that of FIG. 2 showing primary and secondary collimators forming part of a scanner according to a second embodiment of the invention.

Referring to FIG. 4, in a further embodiment of the invention a fixed primary collimator 42A is provided and a single secondary collimator part 42B is pivotably mounted such that it can rotate about a lower corner 44 under the control of a suitable actuator mechanism 46, such as a lead-screw arrangement acting between rotating bearings. The design recognises that the top part of an item such as a vehicle is typically loaded less heavily than the base part of an object. Therefore, a high dose is always provided to the heavily loaded base part of the object with a lower dose being provided to the upper part of the object.

Figure 5:
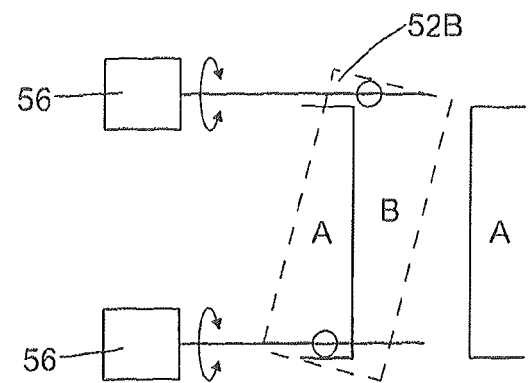
FIG. 5 is a view similar to that of FIG. 2 showing primary and secondary collimators forming part of a scanner according to a further embodiment of the invention.

As an extension to the simplified design shown in FIG. 4, FIG. 5 shows an embodiment with one secondary collimator part 52B that is actuated independently at top and bottom by respective actuators 56. This provides the same effect at the secondary collimator shown in FIG. 2, but with only half the complexity.

Figure 6A:
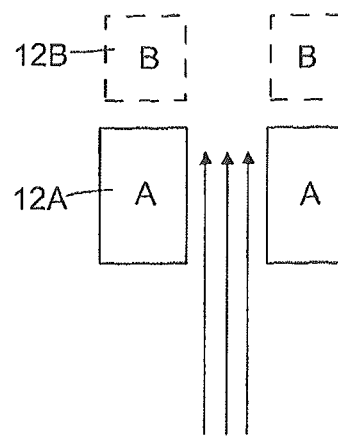
FIG. 6a is a plan view of the collimators forming part of a scanner of FIG. 5.
Figure 6B:
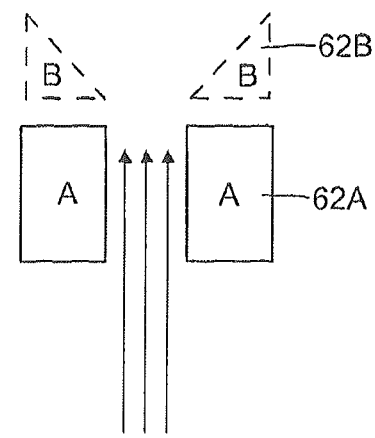
FIG. 6b is a plan view of the collimators of a scanner according to a further embodiment of the invention.

Sometimes, it is prudent to provide a graded dose rate from maximum to zero and all levels in between. To achieve this, an alternative to using a blocking secondary collimator with rectangular cross section, like that of FIG. 2 which is shown in FIG. 6a, is to use a partially transparent secondary collimator 62B, as shown in FIG. 6b. Here, a wedge shaped secondary collimator 62B, tapered so that it gets narrower towards its cut-off edge which defines the edge of the beam, is shown which can be slid across the aperture of the primary collimator 62A in order to provide a gradual variation in dose rate at all parts of the image. In an X-ray or gamma-ray based imaging system, this collimator can advantageously be made from a relatively low attenuation material, such as aluminum, or a more attenuating material, such as copper or steel. In this embodiment the secondary collimator 62B provides the further benefit of modulating the effective energy spectrum of the radiation beam. The higher the effective energy of the radiation spectrum the more penetrating the beam when compared to a lower effective energy beam for equivalent dose. The greater the thickness of the collimator through which the beam passes, the higher the mean energy of the beam that has passed through it.

Figure 7:
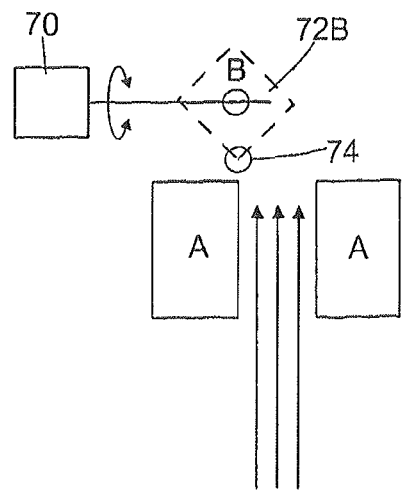
FIG. 7 is a plan view of a collimation system forming part of a scanner according to a further embodiment of the invention.

Referring to FIG. 7, in a refinement of this embodiment, a secondary collimator 72B of rectangular section is pivotally mounted so that it may be rotated about a vertical axis into the beam about one corner 74 by an actuator 70. This gives a widely variable filtering collimator thickness which can be used to good effect in optimising an imaging system. This rotation actuated motion may be combined with a second translation actuated motion, provided for example by a sliding mounting similar to that of FIG. 2 and separate linear actuators, to provide varying filtering along the length of the collimator section.

Referring to FIG. 8, a more complex collimator according to a further embodiment comprises multiple independently actuated collimator sections 82B forming one side of the secondary collimator, which can provide an enhanced level of dose control and reduction using rectangular section and wedge section collimators. Five collimator sections 82B are shown here, but other numbers can of course be used to provide more or less variability. Referring to FIG. 8a, the collimator sections 82b can be rectangular in cross section, or, as shown in FIG. 8b, they can be tapered in a similar manner to those of FIG. 6b. Generally, the upper collimator sections 82U will restrict the dose considerably while the middle and lower collimator sections 82M, 82L will restrict the dose less. However the independently controllable collimator sections mean that the profile of the radiation dose can be varied to any required shape over the height of the fan beam. The actual collimator settings are controlled by the decision processor based on immediate feedback from the image data itself as described above. As shown in FIG. 9, the width, W, of the upper, U, middle, M, and lower, L, collimator sections is continuously variable based on the properties of the object under inspection as determined from analysis of the image data by the decision processor.

Figure 10:
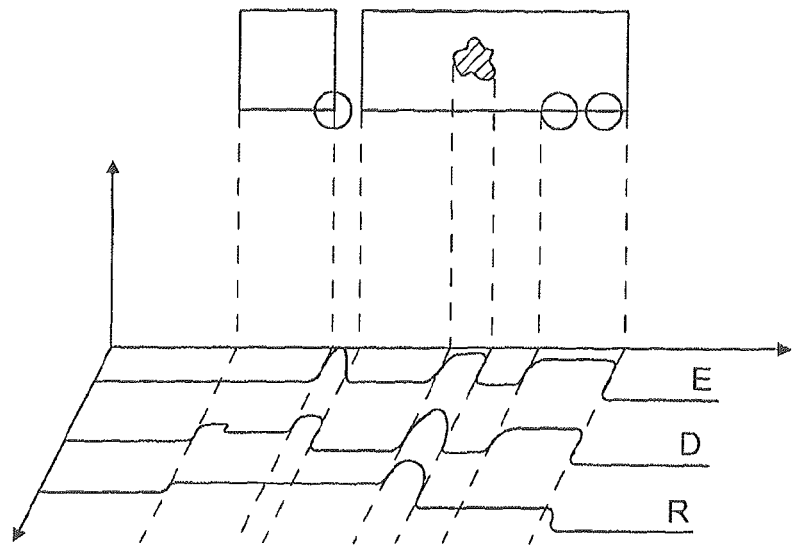
FIG. 10 is a diagram showing how other X-ray beam qualities (E=Energy, D=Dose, R=Rate at which X-ray pulses are generated) can be varied to assist in X-ray system optimisation.

As a further aspect of this embodiment, as with the other embodiments, the properties of the X-ray source may also be varied in a dynamic fashion based upon the properties of the object as recorded at each location and determined by the decision processor. FIG. 10 shows how the energy, E, instantaneous dose rate, D, and pulse rate, R, (where applicable) of the radiation source can be varied in response to an object of variable composition and hence variable attenuation. As with the collimator width, these parameters can be varied in response to changes in total attenuation (or intensity), or changes in the variation in intensity within one linear image data set.

The energy of the X-ray source can be varied in many ways. For example, the energy of an X-ray tube is varied by adjusting the accelerating voltage of the X-ray tube. For a linear accelerator system, there are several ways to change beam energy including varying the RF power which is delivered per pulse (which affects how much acceleration individual electrons will experience), varying the beam current between pulses (which affects the loading of the RF beam and hence the accelerating energy) and varying the electron gun voltage (and hence the mean energy of the electrons as they enter the first stages of the accelerator structure). It will be appreciated that these methods will vary the mean energy (or frequency) of the radiation, and may in some cases also, or alternatively vary the energy spectrum of the radiation.

Dose rate of the X-ray source can also be varied in many ways. For example, in an X-ray tube, the filament current can be varied which affects filament temperature and so also the yield of electrons which are available to contribute to X-ray production. In a linear accelerator system, several approaches may be used to control dose rate including variation of the electron gun injection current and variation of the electron beam pulse width.

In a linear accelerator based system, pulse rate may be varied over quite wide settings by simply altering the rate at which the magnetron is energised, and hence the rate at which RF power is propagated into the waveguide. The electron gun pulse rate must be adjusted accordingly.

Figure 11:
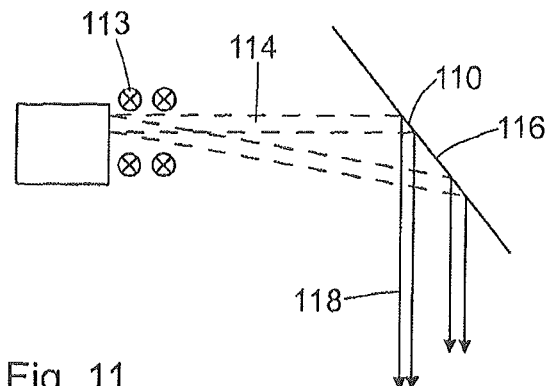
FIG. 11 is a plan view of a scanner system according to a further embodiment of the invention.

Referring to FIG. 11, in a further embodiment of this invention, rather than varying the position of the collimators to vary the intensity of the beam, the position of the radiation source point 110 is varied with respect to the fixed primary collimators 112A such that more or less of the generated radiation is able to propagate through the collimator to the imaging sensors. No secondary collimators are required in this embodiment, although fixed ones may be provided. As an example, in one embodiment a magnet is placed such that a parallel magnetic field 113 is created in the vertical direction such that the focused electron beam 114 in an X-ray tube or linear accelerator system is deflected in the horizontal plane away from its normal path. If the primary collimators 112A are positioned such that the X-ray source electron beam 114, in the absence of a magnet, fires to a point 110 on the target 116 which is centred on the opening of the primary collimator 112A, then as the magnetic field is increased, the focal spot will move out of the central line of the collimator 112A to a point where increasingly less radiation 118 from the source is able to pass though the collimator 112A and the effective instantaneous dose rate falls. In the embodiment of FIG. 11 the target is shown as being at 45° to the electron beam, and the X-rays as being emitted at 90° to the electron beam. However in many high energy X-ray systems the surface of the target is perpendicular to the electron beam and the X-rays are emitted parallel to, and in the same direction as, the electron beam in a 'straight through' arrangement. It will be appreciated that the electron beam in such a system can be controlled in the same was as in the system of FIG. 11 to control the X-ray beam.

Referring to FIGS. 11a, 11b, 11c and 11d, in an alternative configuration, a magnet 113a is positioned with a quadrupole magnetic field along the axis of the electron beam 114a trajectory, such that varying the magnetic field can vary the degree of focussing of the electron beam. At an optimal magnetic field, the electron beam 114a will be focussed at the target 116a to a diameter which is matched by the width of the primary collimator 117a slot width, as shown in FIGS. 11a and 11b. The target in this embodiment is in the straight-through configuration. As the magnetic field is varied away from the optimal point, the focal spot will defocus creating a wider, less intense X-ray beam, and some of the direct focal radiation will be attenuated by the primary collimators 117a, as shown in FIGS. 11c and 11d. To maintain spatial resolution in the imaging system, a separate collimator 119a can be placed defining a slot extending in a direction perpendicular to that of the primary collimator 117a and proximate to the X-ray focal spot 110a. This ensures that the size of the collimated X-ray beam does not increase as the electron beam is de-focussed, thereby minimising apparent focal broadening.

In an alternative embodiment, both the focal spot position and the focal spot size can be modulated simultaneously to provide a wide degree of control of the effective dose rate at the input to the imaging system.

Figure 12:
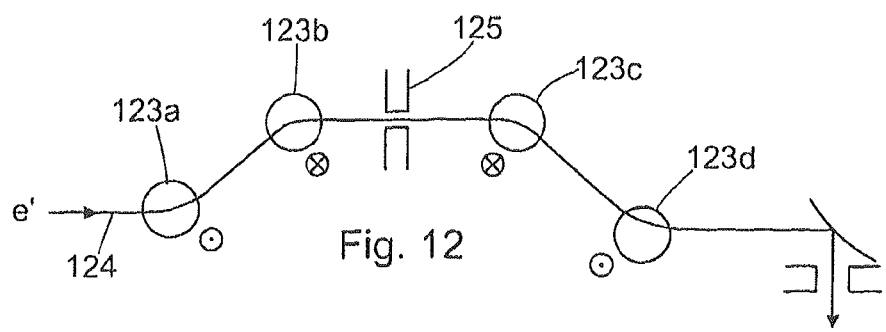
FIG. 12 is a plan view of a scanner system according to a further embodiment of the invention.

Referring to FIG. 12, in a further embodiment, the intensity and energy of the X-ray beam is modulated by blocking a variable proportion of the electrons from the electron beam in the X-ray source. In this embodiment a set of four magnetic dipoles 123a, 123b, 123c, 123d with the first and fourth having one field polarity and the second and third having the opposite polarity such that they first bend the electrons 124 away from their initial path and then into an offset path parallel to the first, then back towards the original path and then back into the initial path. Such a device is usually called a chicane. Note that the electron beam 124 does not necessarily have to come out in the same direction as it went in, and a different direction can be produced by adding a constant fixed field. Important, however, is that the final beam axis has to be independent of the changes in chicane magnetic field strength. Scrapers 125 in the diverted, offset part of the path can be used to remove electrons from the beam 124, thereby changing the intensity. The chicane magnetic field strength 123 determines how far the beam departs from the nominal path, and therefore how many electrons are scraped away. Changing the magnet field strength 123 therefore modulates the intensity of the electron beam 124, and hence also of the X-ray beam 128 it generates on hitting the target 126.

A disadvantage of such a device is that it is likely to take up significant space. However, if the overall beam path is not straight, it allows one to mount the accelerator at an angle. An advantage is that the chicane can be used to make the electron beam more uniform in shape and energy: it functions as an analyzing (set of) magnet(s) because the turning radius, and hence turning angle, of the electrons in the magnetic field is proportional to their energy. This means that with appropriate positioning of the scraper, for example between the second and third magnetic fields 123b, 123c, where the electron beam has been dispersed on the basis of electron energy, the higher or lower energy electrons can be removed from the beam. One can therefore use this method to more accurately determine the actual beam energy. Note that adjusting the magnetic field will allow electrons of a slightly different energy to pass the scraper. Taking into account the very small magnetic field adjustments discussed here, and assuming a relatively mono-energetic electron beam to start with, this is not a large effect.

Trying to do any of this with a dual-energy machine is more complicated, since the desired fields for the two energies are different. However, "kicker-magnets" can change fields very precisely in very short times.

Figure 13:
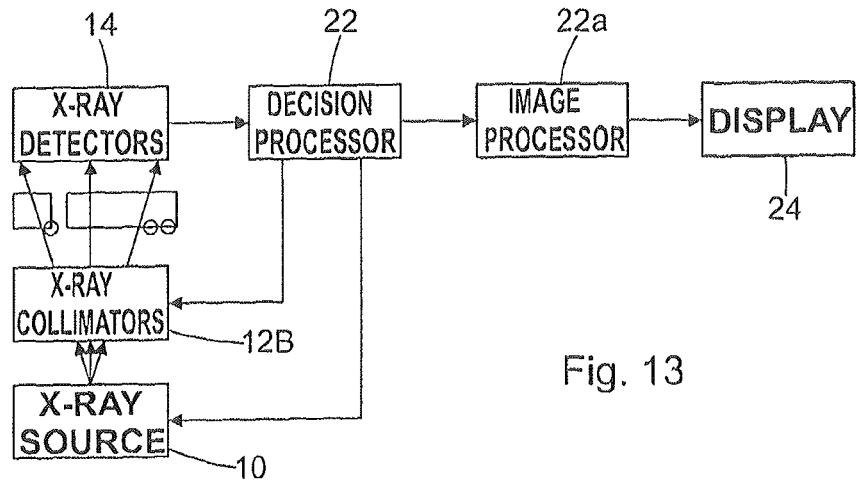
FIG. 13 is a diagram of a processing chain of a scanning system according to an embodiment of the invention.

FIG. 13 shows the signal processing chain which is required to independently control the system collimation, the radiation source and the displayed image. It will be described as part of the system of FIGS. 1 and 2 but would be similar for other embodiments described. The signal processing chain has at its heart the decision processor 22 whose task is to extract data from the imaging signal, to dynamically optimise the radiation source 10 and settings of the secondary collimator 12B and to process the image for optimal display on the display 24. Image processing 22a is shown as a separate functional block, but can be performed by the same processor as the decision processing function, or a different one.

Figure 14:
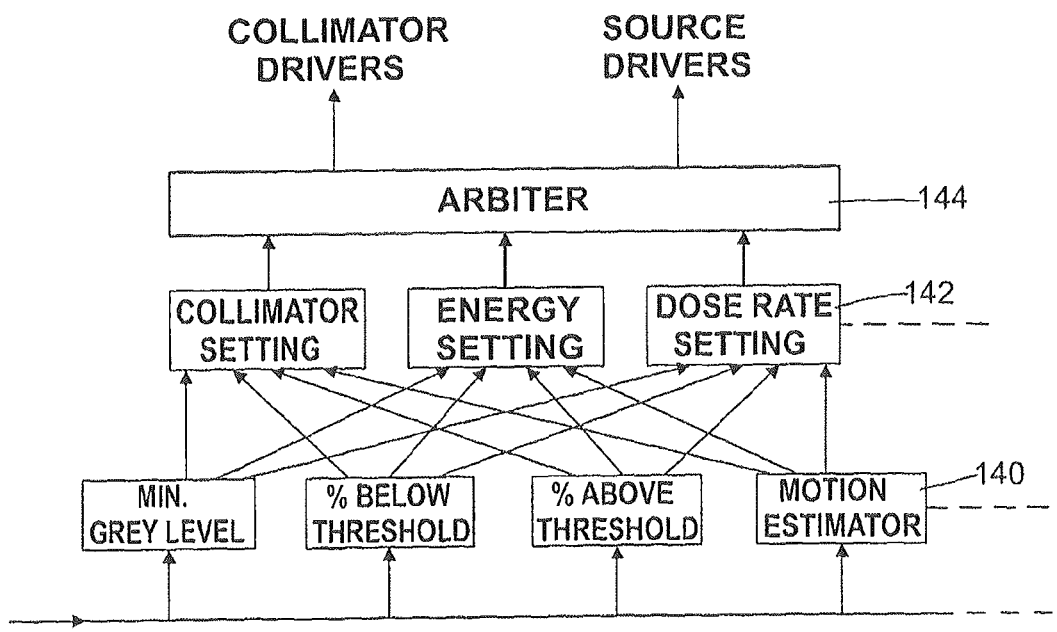
FIG. 14 is a simplified functional block diagram of the decision processor of the system of FIG. 13.

The decision processor architecture of this embodiment is shown in FIG. 14 and uses a rule based optimisation criterion. It comprises low level processing elements 140, higher level processing elements 142 arranged to receive the outputs from the low level elements 140, and a final arbiter arranged to receive the outputs from the higher level processing elements and out put final drive signals to the collimator actuators and the radiation source. Here, input data, which is in the form of a set or row of intensity values making up the image data from the detectors 14, is passed to the low level signal processing elements 140 which each extract certain specific parameters from the newly arrived column of image data. The decision processor 22 is therefore arranged to control the X-ray source on the basis of these parameters, subject to the processing of the higher level processors 142. Useful parameters include the minimum signal intensity or grey level in the data set (if that is too low, then the processor 22 is arranged to increase the net signal at the detector array 14 by opening the secondary collimator 12A or increasing the source dose rate and/or pulse rate), the percentage of the data which lies below a programmable threshold (if the percentage reaches a predetermined threshold, then the processor is arranged to increase the dose rate, the collimator width and/or the beam energy), the percentage of the data which lies above a programmable threshold (if this percentage reaches a predetermined threshold, the processor is arranged to decrease the collimator width, reduce the dose rate and/or beam energy) and the amount of variation in the signal (the more variation in signal column to column, and/or within each column, the more complex the image and therefore the more the processor is arranged to increase the collimator width, the dose rate and/or the beam energy to improve the quality of the recorded image).

The outputs from the low level parameter blocks 140 are then input to the higher level processor blocks 142 which focus on independent optimisation of the main system variables (collimators, radiation source settings and image processing methods). The recommendations output from these high level blocks 142 are then input to the final arbitration processor 144 which determines the final settings for the radiation source, radiation collimators and image processing methods. This final stage is necessary since, if taken on their own, the net effect of each sub-system could result in over optimisation of the system.

In a further aspect of this invention, the image processing applied to the displayed image is selected to produce, in one instance, the most pleasing visual appearance to the image, and, in another instance, the most useful form of the image for threat detection analysis. The two instances may not yield the same image: a threat detection algorithm may have different image requirements than those of visually presenting the results to the operator.

Firstly, the image processor is arranged to calibrate each data element, i.e. each detector intensity value, individually to reflect the actual dose delivered at that point in the image and to compensate for the controlled changes in radiation beam energy across the image. A suitable mechanism for calibrating the image is to apply non-linear gain and offset compensation using a non-linear calibration curve derived from the equivalent beam quality (or energy) for each source and equivalent beam filtration. It is beneficial to parameterise these curves as a function firstly of effective radiation beam quality and secondarily on effective collimator thickness to achieve a calibration factor of the form:

$$I_C = I_M^2 F_2(E, C) + I_M F_1(E, C) + I_0$$

where $I_c$=corrected pixel intensity, $I_m$=measured pixel intensity, $F_2(\ )$=second order correction factor based on Energy and Collimator setting (width and/or thickness), $F_1(\ )$=first order correction factor based on Energy and Collimator setting and $I_0$=offset correction factor. Higher order corrections may be applied as needed. Such an approach normalises the intensities in the image and provides a much more smooth (less stripy) image, particularly in regions of high attenuation.

Secondly, it is beneficial to correct for scattering effects which occur around dense objects where a "halo" effect can be observed due to excess scatter at neighbouring detection elements arising from scattering at the edges of the dense object.

Thirdly, image colouring may be applied to those regions of particularly high attenuation where image optimisation at the level required may not have been possible given the physical constraints of the radiation source and collimation systems. For example, in highly attenuating regions, it may not be possible to get sufficient penetration through the object to get the detector to respond within its linear or low-noise region. Such regions can be coloured with a particular colour, the colour reflecting the severity of the optimisation error.

Figure 15:
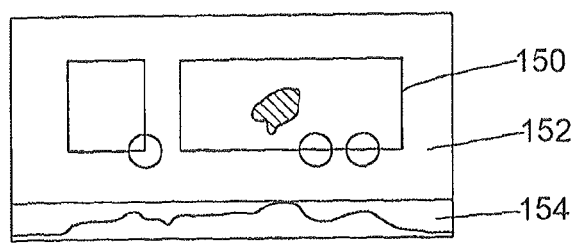
FIG. 15 shows a display generated by the system of FIG. 8

Fourthly, a graphical representation of the optimisation result may be displayed on the inspection screen adjacent to the X-ray image, for example as shown in FIG. 15. Here, the radiation image 150 is displayed on the top part of the screen 152 and the effective dose rate is displayed as a graph 154 at the bottom of the screen. Alternatively, the optimisation result may be displayed using blocks of colour that fill the band at the bottom of the inspection screen—a hot wire spectrum would show low dose regions in dark red with highest dose regions in white and intermediate dose regions in a light orange, for example.

Fifthly, especially for threat detection analysis, in high-attenuation regions, multiple pixels may be combined into larger pixels, in order to extract statistically significant penetration measurements. These larger pixels may or may not be presented visually to the operator.

Dual-energy scanning is a method used to distinguish materials with atomic numbers (Z) in different ranges; for example organic materials from steel-copper, and these from very high Z, such a uranium and plutonium. A dual energy system according to an embodiment of the invention includes a radiation generator arranged to generate two radiation beams, one of higher energy than the other. The noise in the image, and therefore the penetration, is dominated by the lower transmission of the low-energy beam. Increasing the x-ray source output of both energies, in most cases, will increase penetration, but will also increase the dose to the cargo and vicinity. However, the decision processor in such an embodiment is arranged to control the output of the low-energy beam so that increase to the point that the noise contribution of the low- and high-energy beams is approximately the same. This can minimize the dose exposure. The ratio of the low- and high-energy beam outputs is determined by determining the noise levels in the transmitted image and adjusting one or both of the beams accordingly employing one or more of the above described methods until the desired noise levels are achieved.

Some embodiments of the invention are arranged for sea cargo scanning, which requires inspection of only the sea containers. However, checkpoints such as land crossing require inspecting, in addition to the trailer, the cabin which is occupied by the driver and possibly passengers. To avoid radiation exposure to the occupants, sometimes the cabin is not inspected, obviously leaving a gap in the inspection process. Other methods include making the occupants exit the vehicle and employing a gantry configuration or using a towing arrangement to inspect the entire truck. Another existing method employs a low-energy beam to inspect the cabin including its occupants.

In some embodiments of this invention one or more of the approaches described above is employed to reduce the dose to the occupants. The dose profile can be fine tuned to deliver a higher dose to the engine and a much lower dose in the area where the driver and passenger(s) are, and an increasing dose as the beam plane moves away from the occupants. The dose profile is optimized for maximum penetration while maintaining a dose exposure, due to direct exposure and beam scatter, to the passengers that meets regulatory limits.

Cargo is typically loaded with heavier cargo placed at the bottom. Many cargos, in particular heavy loads are not packed to the height of the container or trailer. In addition, the x-ray output required for penetrating the flatbed or bottom of cargo containers is known to be within some specific range. In these and other cases, the height-dependent collimators are adjusted to deliver a dose sufficient to penetrate these regions. For example, the collimators could be adjusted to provide a very low dose to the top of the container where there is no cargo.

It will be appreciated that the invention can also be used with systems using Continuous Wave (CW) X-ray sources (i.e. sources which produce X-rays continuously, as opposed to pulsed sources), betatrons, etc and to other types of radiation sources such as radio-isotopic sources and neutron generators.

Figure 16:
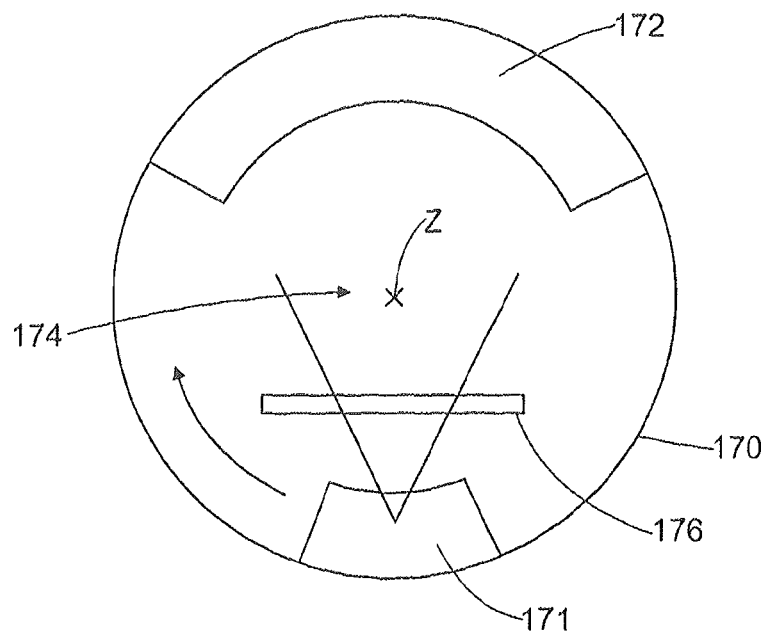
FIG. 16 is a section through a CT scanner according to a further embodiment of the invention.
Figure 17:
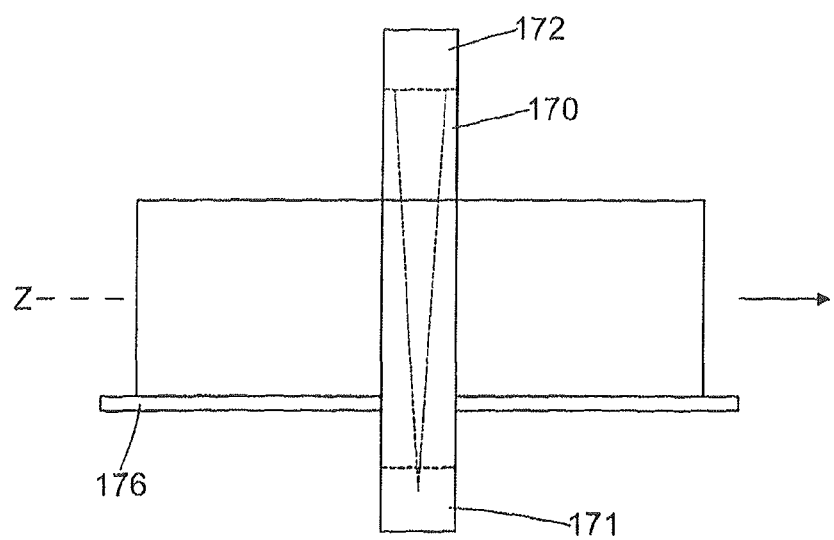
FIG. 17 is a side view of the scanner of FIG. 16.

Referring to FIGS. 16 and 17 a medical CT scanner according to a further embodiment of the invention comprises a rotating gantry 170 supporting an X-ray source 171 and detector array 172. The gantry 170 can be rotated about an axis Z so as to gather data for a two dimensional image slice of an imaged volume 174. A support 176 is arranged to support a patient, and to move the patient along the axial direction through the scanning volume 174 in steps. At each step the gantry is rotated and a further 2D image data set is gathered. The X-ray source 171 is controlled by a processor unit 178 which is arranged to analyse each 2D data set and generate an output signal which is sent to the source 171 to vary the output of the source 171 for the next step if the data in one 2D image data set (or a group of data sets) does not meet a required condition. In this case the condition can be the absence of artifacts in the image. As is well known, if the level of radiation at the detector array 172 is too low, then artifacts will be present in the image generated from the detector data. If a further condition is defined, such as a maximum total image intensity, which if exceeded causes the processor unit 178 to reduce the radiation output, this system can operate to scan an entire patient whilst keeping the radiation at approximately the minimum level required to obtain an artefact-free image. This has many benefits including minimizing the dose to the patient, and minimizing the amount of shielding required around the scanner.

We claim:

1. A scanner system comprising:
   a radiation generator arranged to generate radiation to irradiate an object, having a velocity, wherein the radiation generator comprises an adjustable collimator and wherein the object comprises areas of a first attenuation level and areas of a second attenuation level, said first attenuation level being higher than said second attenuation level;
   a detector structure arranged to detect the radiation after it has interacted with the object and generate a sequence of detector data sets as the object is moved relative to the generator; and
   a processor arranged to obtain and process each of the detector data sets thereby to generate a control output arranged to adjust the collimator and subsequently vary the radiation from the radiation generator as the object is scanned, wherein the processor is arranged to modulate a rate at which the data sets are obtained such that said rate varies with the velocity of the object and wherein the control output is arranged to adjust the collimator and subsequently vary said radiation such that said radiation comprises a first dose rate and a second dose rate, said first dose rate being higher than said second dose rate, and such that radiation of said first dose rate is directed toward the areas of the first attenuation level and radiation of said second dose rate is directed toward the areas of the second attenuation level.

2. A scanner system according to claim 1 wherein the processor is arranged to define a parameter of the detector data, to determine a value of the parameter for each data set, and generate a control output arranged to vary the radiation output if the value of the parameter does not meet a predetermined condition.

3. A scanner according to claim 1 wherein the detector structure comprises a plurality of detectors and the detector data comprises a set of intensity values indicative of the intensity of radiation at each of the detectors.

4. A scanner system according to claim 1 wherein the control output is arranged to control the energy of the radiation.

5. A scanner system according to claim 1 wherein the control output is arranged to control a dimension of the radiation beam.

6. A scanner system according to claim 1 wherein the radiation generator is arranged to generate the radiation in pulses and the control output is arranged to control at least one of the duration and the frequency of the pulses.

7. A scanner system according to claim 1 wherein the collimator has a varying thickness so that adjustment of the collimator can adjust the energy of the radiation beam.

8. A scanner system according to claim 1 wherein the collimator comprises a plurality of collimator elements each of which can be adjusted independently so as to vary different respective parts of the radiation beam.

9. A scanner system according to claim 1 wherein the control input is arranged to generate the radiation as a beam and to vary the position of the beam in response to the control input thereby to vary the proportion of the beam that is blocked by the collimator.

10. A scanner system according to claim 1 wherein the radiation generator comprises an electron source arranged to direct a beam of electrons towards a target, and is arranged to adjust the electron beam in response to the control input.

11. A scanner system according to claim 10 wherein the radiation generator includes a scraper arranged to block a variable proportion of the electrons in the beam.

12. A scanner system according to claim 11 wherein the radiation generator is arranged to generate a magnetic field and to direct the electron beam through the magnetic field so that it turns, and wherein the magnetic field is variable to vary the proportion of the electrons which are blocked.

13. A scanner system according to claim 10 wherein the radiation generator is arranged to generate a variable magnetic field and to vary the magnetic field so as to vary focusing of the electron beam.

14. A scanner system according to claim 1 wherein the processor is arranged to adjust the detector data to compensate at least partially for the controlled variation of the radiation output.

15. A scanner system according to claim 1 wherein the radiation generator and the detection structure are supported on a rotatable gantry which is arranged to rotate as each data set is collected.

* * * * *